(12) United States Patent
Jackson et al.

(10) Patent No.: US 11,029,304 B2
(45) Date of Patent: Jun. 8, 2021

(54) WATER RETORT

(71) Applicant: Halliburton Energy Services, Inc., Houston, TX (US)

(72) Inventors: Brice Aaron Jackson, Houston, TX (US); Kevin G Kleinguetl, Kingwood, TX (US); Adam Dotson, Houston, TX (US); Dale E Jamison, Humble, TX (US); Lawrence Joseph Herskowitz, Pearland, TX (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 245 days.

(21) Appl. No.: 16/344,342

(22) PCT Filed: Jul. 18, 2018

(86) PCT No.: PCT/US2018/042733
§ 371 (c)(1),
(2) Date: Apr. 23, 2019

(87) PCT Pub. No.: WO2020/018093
PCT Pub. Date: Jan. 23, 2020

(65) Prior Publication Data
US 2020/0386735 A1    Dec. 10, 2020

(51) Int. Cl.
*G01N 33/28* (2006.01)
*E21B 21/01* (2006.01)
(Continued)

(52) U.S. Cl.
CPC ......... *G01N 33/2847* (2013.01); *E21B 21/01* (2013.01); *E21B 49/086* (2013.01);
(Continued)

(58) Field of Classification Search
CPC ...... G01N 33/2847; G01N 1/44; G01N 25/18; G01N 33/2823; E21B 21/01; E21B 49/086; E21B 49/005; G01F 22/00
See application file for complete search history.

(56) References Cited

U.S. PATENT DOCUMENTS 2,723,228 A    11/1955  Moore et al.
8,817,241 B2   8/2014   LaFrancois et al.
(Continued)

FOREIGN PATENT DOCUMENTS

WO    2016105391 A1    6/2016

OTHER PUBLICATIONS

International Search Report and Written Opinion dated Apr. 16, 2019; International PCT Application No. PCT/US2018/042733.

*Primary Examiner* — Benjamin R Schmitt
(74) *Attorney, Agent, or Firm* — McguireWoods, LLP

(57) ABSTRACT

Provided is a water retort apparatus, methods of using the water retort apparatus, and systems including the water retort apparatus. An example of the water retort apparatus comprises a sample test cell, a heating element configured to heat the sample test cell to a temperature between about 212° F. and about 400° F., a condenser in fluidic communication with the sample test cell, a sight glass in fluidic communication with the condenser, a camera configured to capture images of the sight glass, and a controller configured to analyze the images captured by the camera and estimate a volume of water in the sight glass.

20 Claims, 4 Drawing Sheets

(51) Int. Cl.
  *E21B 49/08* (2006.01)
  *G01F 22/00* (2006.01)
  *G01N 1/44* (2006.01)
  *G01N 25/18* (2006.01)

(52) U.S. Cl.
  CPC ............... *G01F 22/00* (2013.01); *G01N 1/44* (2013.01); *G01N 25/18* (2013.01); *G01N 33/2823* (2013.01)

(56) References Cited

U.S. PATENT DOCUMENTS

| | | |
|---|---|---|
| 2008/0283296 A1 | 11/2008 | Zamora et al. |
| 2013/0277113 A1 | 10/2013 | Murphy |
| 2014/0260561 A1 | 9/2014 | Brost et al. |
| 2015/0300997 A1* | 10/2015 | Kriel .................. G01N 33/2823 73/23.42 |
| 2016/0258279 A1 | 9/2016 | Xia et al. |
| 2017/0122891 A1 | 5/2017 | McCarthy et al. |
| 2017/0342812 A1* | 11/2017 | Kuhn .................. B01D 17/044 |

\* cited by examiner

WATER RETORT

TECHNICAL FIELD

The present disclosure relates to an apparatus for performing a water retort and a method of using the same, and more particularly, to utilizing a water retort test to monitor the water volume in a drilling fluid sample.

BACKGROUND

During the drilling of a wellbore, a drilling fluid, also referred to as a drilling mud, may be continuously circulated in the wellbore. The drilling fluid serves several purposes, including providing sufficient hydrostatic pressure to prevent formation fluids from entering the wellbore, cooling and cleaning the drill bit, circulating drill cuttings and debris out of the drilled wellbore, and suspending the drill cuttings while drilling is paused or while the drilling assembly is brought in and out of the wellbore. It is often desirable to analyze the drilling fluid to determine the percentages of the water, oil, and solids contained therein. Determining the water, oil, and solids content may be useful for an efficient drilling operation. For example, operators may use the water, oil, and solids content to determine the efficacy of the solids control equipment, changes to the downhole formation, and filtration characteristics or requirements, etc.

Typically, the water, oil, and solids content may be measured using a technique called a mud retort. A mud retort uses a distillation unit to heat and then separately distill the water and oil from a drilling fluid sample, leaving any solids behind in the process. The volume fraction of the water, oil, and solids content may then be determined. Provided are improved apparatuses and methods for measuring the water volume of a drilling fluid sample.

BRIEF DESCRIPTION OF THE DRAWINGS

Illustrative examples of the present disclosure are described in detail below with reference to the attached drawing figures, which are incorporated by reference herein, and wherein.

Figure 1:
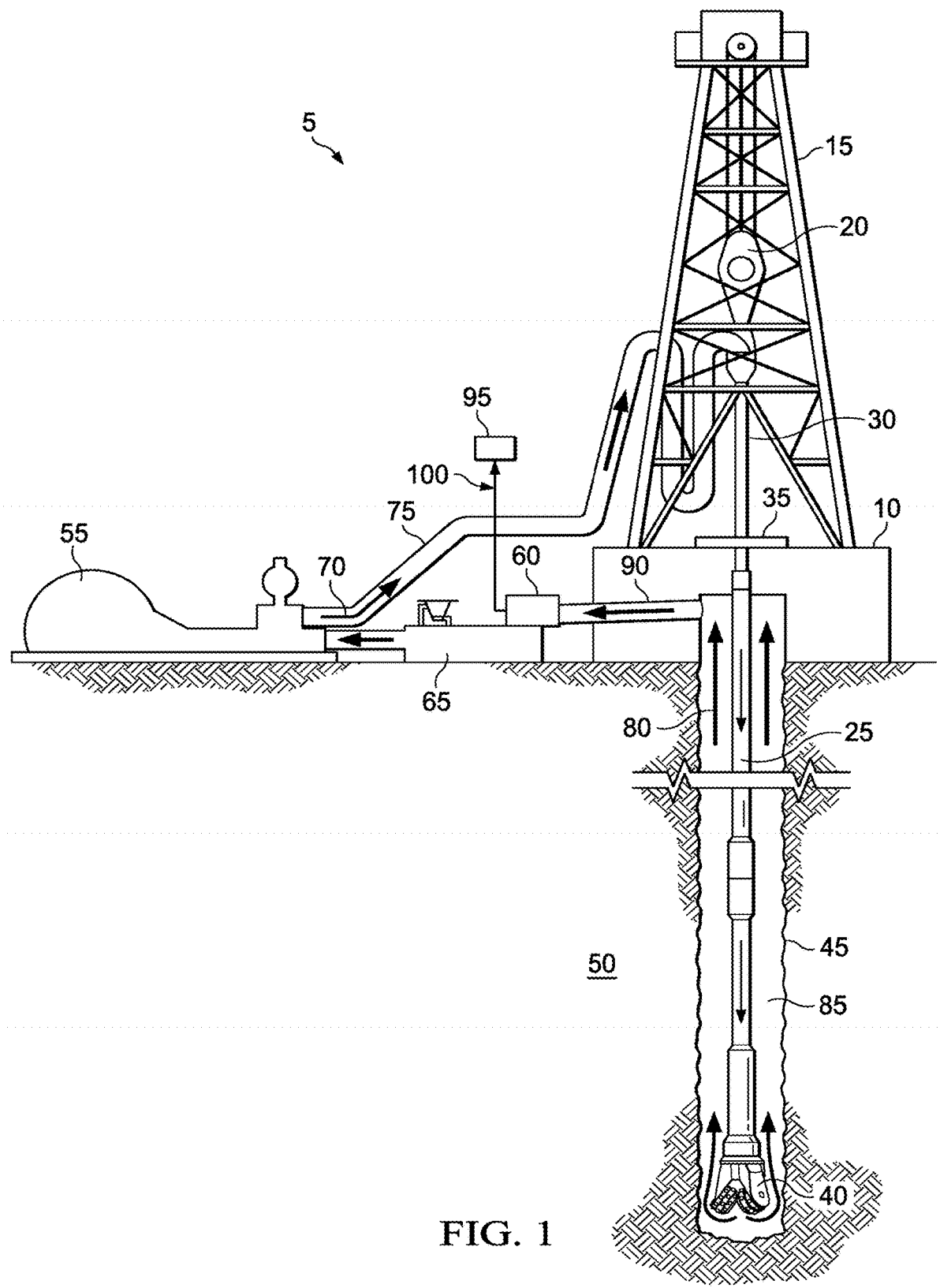
FIG. 1 is a schematic of an example drilling system in accordance with one or more examples described herein.

The illustrated figures are only exemplary and are not intended to assert or imply any limitation with regard to the environment, architecture, design, or process in which different examples may be implemented.

DETAILED DESCRIPTION

The present disclosure relates to an apparatus for performing a water retort and a method of using the same, and more particularly, to utilizing a water retort test to monitor the water volume in a drilling fluid sample.

In the following detailed description of several illustrative examples reference is made to the accompanying drawings that form a part hereof and in which is shown by way of illustration specific examples that may be practiced. These examples are described in sufficient detail to enable those skilled in the art to practice them, and it is to be understood that other examples may be utilized and that logical structural, mechanical, electrical, and chemical changes may be made without departing from the spirit or scope of the disclosed examples. To avoid detail not necessary to enable those skilled in the art to practice the examples described herein, the description may omit certain information known to those skilled in the art. The following detailed description is, therefore, not to be taken in a limiting sense, and the scope of the illustrative examples are defined only by the appended claims.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the examples of the present invention. At the very least, and not as an attempt to limit the application of the doctrine of equivalents to the scope of the claim, each numerical parameter should at least be construed in light of the number of reported significant digits and by applying ordinary rounding techniques. It should be noted that when "about" is at the beginning of a numerical list, "about" modifies each number of the numerical list. Further, in some numerical listings of ranges some lower limits listed may be greater than some upper limits listed. One skilled in the art will recognize that the selected subset will require the selection of an upper limit in excess of the selected lower limit.

Unless otherwise specified, any use of any form of the terms "connect," "engage," "couple," "attach," or any other term describing an interaction between elements is not meant to limit the interaction to direct interaction between the elements and may also include indirect interaction between the elements described. Further, any use of any form of the terms "connect," "engage," "couple," "attach," or any other term describing an interaction between elements includes items integrally formed together without the aid of extraneous fasteners or joining devices. In the following discussion and in the claims, the terms "including" and "comprising" are used in an open-ended fashion, and thus should be interpreted to mean "including, but not limited to." Unless otherwise indicated, as used throughout this document, "or" does not require mutual exclusivity.

The terms uphole and downhole may be used to refer to the location of various components relative to the bottom or end of a well. For example, a first component described as uphole from a second component may be further away from the end of the well than the second component. Similarly, a first component described as being downhole from a second component may be located closer to the end of the well than the second component.

The examples disclosed herein comprise a water retort apparatus, methods of use, and systems comprising the water retort apparatus. The water retort apparatus may be used to measure the water content of a drilling fluid recovered from a wellbore. The "water," as used herein, may be from the drilling fluid, for example, if the drilling fluid is a water-based mud ("WBM"), where water is the continuous phase and an oil, or other non-miscible material, is the internal phase; or the "water" may also be native to the subterranean formation, for example, water present within the subterranean formation being drilled into. The "water" may also come from other treatment or wellbore fluids introduced into the wellbore and/or the subterranean formation. Likewise, the "oil," as used herein, may be from the drilling fluid, for example, if the drilling fluid is an oil-based mud ("OBM"), where oil is the continuous phase and water, brine, or other non-miscible material is the internal phase; or the "oil" may also be native to the subterranean formation, for example, hydrocarbons present within the subterranean formation being drilled into. The "oil" may also come from other treatment or wellbore fluids introduced into the wellbore and/or subterranean formation. "Solids," as used herein, refers to any solids recovered from a wellbore, which may include solids removed from the surface of a wellbore or solids removed from within a wellbore. Examples of solids may include, but should not be limited to, drill cuttings, solid drilling fluid additives such as weighting agents, lost-circulation materials, etc.; proppants; solids native to the subterranean formation such as sand, minerals, etc.; or any combinations thereof. As the solids are introduced to and/or circulated within the wellbore, the solids may contact water and/or oil and be contaminated with the water and/or oil.

The water retort apparatus may be used to monitor the water volume in a drilling fluid sample. The measurement of the water volume may minimize or exclude oil from the final volume measurement so as to give an accurate reading as to the water volume measurement. One of the many potential advantages of the water retort apparatus is that very little, if any, oil is vaporized. If a small volume of oil is vaporized, the distillation technique and plumbing of the water retort apparatus may be constructed so as to exclude the oil from the water volume measurement. As such, the sample test cell of the water retort apparatus does not need to be heated to the vaporization temperature of the oil, which in turn reduces the time needed to heat the sample test cell to perform the retort test. A further advantage is that the solids within the drilling fluid sample stay suspended in the oil within the test cell as the oil is not vaporized and the solids are not vaporized or sublimated. This reduces the time necessary to clean the sample test cell of the water retort apparatus as the suspended solids are generally easier to remove from the test cell than the dried solids that would remain after vaporization of the oil. Moreover, the reduced vaporization temperature of the water retort apparatus prevents dried soot from the deposition of any gaseous solids from forming in the tubing and condenser of the water retort apparatus. As such, the piping and other components of the water retort apparatus may be cleaned simply by introduction of a gas such as nitrogen, which may be used to remove trapped water vapor from the piping and other components of the water retort apparatus. Due in part to these noted advantages, an additional advantage of the water retort apparatus is that it may be used to run subsequent test samples very quickly. Moreover, the water retort apparatus may be designed to maintain the elevated water vaporization temperature as well as to automate the cleaning process while maintaining said temperature. These additional innovations may further reduce the time needed to test subsequent test samples. Yet another advantage is that the water retort apparatus may utilize an automated measurement system that estimates the water volume measurements without reliance upon human measurement. This automated measurement system may shorten experiment time by estimating the final measurement result. A still further advantage is that the water retort apparatus may be modified to determine the oil and/or solids content of the oil and solids remaining in the sample test cell. For example, the thermal conductivity of the oil and solids content may be measured and used with the water volume measurement to determine an oil to water ratio of the drilling fluid sample.

FIG. 1 is a schematic of an example drilling system, generally 5, which may make use of the water retort apparatus 95 for analysis of the water content of a circulated drilling fluid 80. It should be noted that while FIG. 1 depicts a land-based drilling system, those skilled in the art will readily recognize that the principles described herein are equally applicable to subsea drilling operations that employ floating or sea-based platforms and rigs, without departing from the scope of the disclosure. As illustrated, the drilling system 5 may include a drilling platform 10 that supports a derrick 15 having a traveling block 20 for raising and lowering a drill string 25.

The drill string 25 may include, but is not limited to, drill pipe and coiled tubing, as is generally known to those skilled in the art. A kelly 30 may support the drill string 25 as it may be lowered through a rotary table 35. A drill bit 40 may be attached to the distal end of the drill string 25 and may be driven either by a downhole motor and/or via rotation of the drill string 25 from the well surface. Without limitation, the drill bit 40 may include roller cone bits, PDC bits, natural diamond bits, any hole openers, reamers, coring bits, and the like. As the drill bit 40 rotates, it may create a wellbore 45 that penetrates various subterranean formations 50.

The drilling system 5 may further include a mud pump 55, one or more solids control systems 60, and a mud pit 65. The mud pump 55 representatively includes any conduits, pipelines, trucks, tubulars, and/or pipes used to fluidically convey a clean drilling fluid 70 downhole; any pumps, compressors, or motors (e.g., topside or downhole) used to drive the clean drilling fluid 70 into motion; any valves or related joints used to regulate the pressure or flow rate of the clean drilling fluid 70, and any sensors (e.g., pressure, temperature, flow rate, etc.), gauges, and/or combinations thereof, and the like. The mud pump 55 may circulate the clean drilling fluid 70 through a feed pipe 75 and to the kelly 30, which may convey the clean drilling fluid 70 downhole through the interior of the drill string 25 and through one or more orifices in the drill bit 40. The now circulated drilling fluid 80 may then be circulated back to the surface via an annulus 85 defined between the drill string 25 and the walls of the wellbore 45. At the surface, the circulated drilling fluid 80 may be conveyed to the solids control system 60 via an interconnecting flow line 90. The solids control system 60 may include various methods and systems for solids control, examples of which may include, but are not limited to, one or more of a shaker (e.g., shale shaker), a centrifuge, a hydrocyclone, a separator (including magnetic and electrical separators), a desilter, a desander, a separator, a filter (e.g., diatomaceous earth filters), a heat exchanger, and any fluid reclamation equipment. Solids control system 60 may remove and separate recovered solids from the circulated drilling fluid 80. After passing through the solids control system 60, a now cleaned drilling fluid 70 may be deposited into a nearby mud pit 65. While illustrated as being arranged at the outlet of the wellbore 45 via the annulus 85, those skilled in the art will readily appreciate that the solids control system 60 may be arranged at any other location in the drilling system 5 to facilitate its proper function, without departing from the scope of the disclosure.

Referring still to FIG. 1, the drilling system 5 may further include a water retort apparatus 95. As illustrated in FIG. 1, the water retort apparatus 95 may, for example, be used to intermittently measure the water volume of the circulated drilling fluid 80. As illustrated, a sample of the circulated drilling fluid 80 may be removed from the solids control system 60, mud pit 65, the interconnecting flow line 90, or from any such component after circulation. The sample of the circulated drilling fluid 80 may be removed from these components prior to or after performing solids removal from the circulated drilling fluid 80 if desired. The sample of circulated drilling fluid 80 may be conveyed to the water retort apparatus 95 via a conveyance means 100. The conveyance means 100 may include any means for transporting a sample of the circulated drilling fluid 80 to the water retort apparatus 95. Examples of the conveyance means 100 may include an operator physically removing a sample and carrying the sample to the water retort apparatus 95. Alternatively, the conveyance means 100 may include a transporting conduit or other transport means that may pump a sample to the water retort apparatus 95. Once the water retort apparatus 95 has finished its operation (described in greater detail below) the remnants of the sample of the circulated drilling fluid 80 may be sent for disposal via any sufficient disposal method. Alternatively, and as described below, additional tests may be done to determine the oil and/or solids content of the sample of the circulated drilling fluid 80. In such optional methods, an oil to water ratio of the drilling fluid may be determined. Afterwards the remnants of the sample of the circulated drilling fluid 80 may then be disposed via the sufficient disposal method. The determined water volume, as well as the oil to water ratio, may be used to modify elements of upstream processes such as the disposal method or downstream processes such as solids control operations if desired.

Although the drilling system 5 depicted in FIG. 1 illustrates use of the water retort apparatus 95 to test the water volume of a sample of the circulated drilling fluid 80, it is to be understood that the water retort apparatus 95 may be used to test the water content of the drilling fluid at any stage of the process. For example, a sample may be taken from a mud pit. Alternatively, a sample of the clean drilling fluid 70 may be taken from any point in which it may be accessible. The conveyance means 100 may need to be modified accordingly to accommodate samples of the drilling fluid taken from different locations of the drilling system 5.

It should be clearly understood that the drilling system 5 of FIG. 1 is merely one example of an application of the principles of this disclosure in practice, and a wide variety of other examples are possible. Therefore, the scope of this disclosure is not limited at all to the details of FIG. 1 described herein and/or depicted in any of the other FIGURES.

Figure 2:
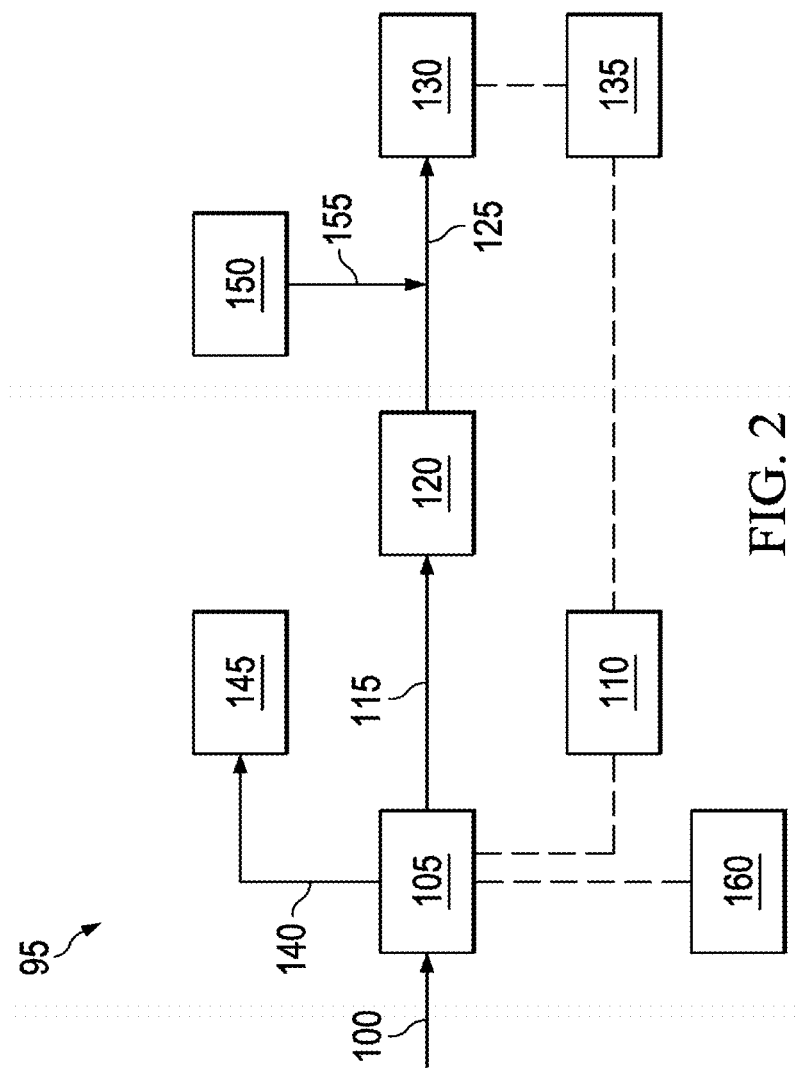
FIG. 2 is a block diagram of the operation and components of the water retort apparatus in accordance with one or more examples described herein.

FIG. 2 is a block diagram of the operation and components of the water retort apparatus 95. The water retort apparatus 95 comprises a sample test cell 105. The sample test cell 105 is a cell of any desirable shape and size, into which the sample of drilling fluid (e.g., the sample of circulated drilling fluid 80 as described in FIG. 1) may be injected. The sample of drilling fluid may be introduced into the sample test cell 105 via the conveyance means 100 as described above, which may comprise injection of the sample by an operator, injection via connected tubing, etc. The sample test cell 105 comprises an opening for injection. The opening may be sealable by a removable threaded cap or other such sealable opening, which may be sealed after injection and during the heating process. In some optional examples, the sample test cell 105 may also comprise a plunger, discussed in greater detail below, which may be used for ejection of the oil and suspended solids after the water has been vaporized from the sample of the drilling fluid. The plunger may be used to clean the sample test cell 105 so that subsequent samples may be tested in the sample test cell 105.

After injection of the drilling fluid sample, the sample test cell 105 is heated to a desired temperature as instructed via a controller 110. Subsequent sample test cells 105 may be used with the water tort apparatus 95 without the need to ramp up the heating of the sample test cell. The controller 110 may set the temperature to any temperature sufficient for vaporization of the water within the sample test cell 105. Although the controller 110 may set the temperature of the sample test cell 105 to any desired temperature, it is to be understood that the set temperature will be less than that of the vaporization temperature of the oil within the drilling fluid sample. In a specific example, the temperature within the sample test cell 105 is set by the controller 110 to be between about 212° F. and 412° F. In a preferred example, the temperature within the sample test cell 105 is about 320° F. The controller 110 may set the temperature of the sample test cell 105 with any sufficient heating element. The heating element may be any heating element sufficient for heating the sample test cell 105 and for raising the temperature of the sample of drilling fluid to the desired temperature sufficient for water vaporization. Examples of the heating element may include heating jackets, hot plates, burners, and the like. The heating element may be coupled to the sample test cell 105 and/or the controller 110. The control of the heating element may be performed manually or automatically. The heating element may be controlled by the controller 110 in examples where the heating element is coupled to the controller 110.

The temperature of the sample test cell 105 may range from about 212° F. to about 400° F. The temperature may range from any lower limit to any upper limit and encompass any subset between the upper and lower limits. Some of the lower limits listed may be greater than some of the listed upper limits. One skilled in the art will recognize that the selected subset may require the selection of an upper limit in excess of the selected lower limit. Therefore, it is to be understood that every range of values is encompassed within the broader range of values. For example, the temperature of the sample test cell 105 may range from about 212° F. to about 400° F., from about 225° F. to about 400° F., from about 250° F. to about 400° F., from about 275° F. to about 400° F., from about 300° F. to about 400° F., from about 325° F. to about 400° F., from about 350° F. to about 400° F., or from about 375° F. to about 400° F. As another example, the temperature of the sample test cell 105 may range from about 212° F. to about 400° F., from about 212° F. to about 375° F., from about 212° F. to about 350° F., from about 212° F. to about 325° F., from about 212° F. to about 300° F., from about 212° F. to about 275° F., from about 212° F. to about 250° F., or from about 212° F. to about 225° F. With the benefit of this disclosure, one of ordinary skill in the art will be readily able to prepare the sample test cell 105 to have a desired temperature for a given application.

As the water evaporates from sample test cell 105, the water vapor is conveyed to tubing 115 via a ventilated connection in or otherwise connected to the sample test cell 105. The tubing 115 allows the water vapor to be conveyed to a condenser 120. The tubing 115 may be sealed to the sample test cell 105 and the condenser 120 to prevent the atmospheric escape of water vapor from the sample test cell 105. Condenser 120 may be used to condense the water vapor to the liquid phase. The condenser 120 may include any type of heat exchanger known in the art for condensing water vapor into the liquid phase. The condenser 120 may be kept at a lower temperature than the water vapor, which may have a temperature at or below that of the heated sample of the drilling fluid. In some examples, the condenser 120 may maintain a temperature close to that of the ambient temperature. In alternative examples, the condenser 120 may maintain a temperature below that of the ambient temperature using a cooling means such as insulation, ice, cooling liquids, fans, etc. The water vapor may be conveyed within a throughbore within the condenser 120. The throughbore may be circuitous or otherwise tortuous in some examples. In other examples, the throughbore may be a direct path through the condenser 120. As the water vapor traverses the condenser 120, the water vapor may condense into its liquid phase. The liquid water may then be discharged from the condenser 120 via a tubing 125 and collected in a sight glass 130. The tubing 125 may be sealed to the condenser 120 and the sight glass 130 to prevent the atmospheric escape of any of the water vapor from the condenser 120 or the sight glass 130.

In some examples, the sight glass 130 may not comprise glass, but instead may comprise a clear polymeric material. In all examples, the sight glass 130 is and/or comprises a clear material such that the sight glass 130 comprises a viewing window sufficient for viewing the volume of the liquid water collected in the sight glass 130. The volume of the liquid water may be measured to determine, for example, the volume of water in the sample of drilling fluid. In examples that do not use a machine vision system, the sight glass 130 may not need to be clear and instead may be any sufficient container for obtaining a volume measurement of the collected liquid water. A camera 135 may view the sight glass 130 to monitor the volume of the liquid water in the sight glass 130 over the operation. The controller 110 may be used to convert the images of the liquid water within the sight glass 130 into a volume measurement. Using a best-fit equation, for example, Equation 1 as discussed below, the controller 110 may be able to estimate the final volume of the liquid water. When the volume value stabilizes, the controller 110 may end the testing operation for a specific sample of drilling fluid. An example best-fit equation is illustrated by Equation 1:

$$V = A(1 - \exp^{(-Bt)}) + C \quad \text{(Eq. 1)}$$

where V is observed volume within the sight glass 130, A is the amplitude of the function, B is the decay factor, C is an offset. It is to be understood that Equation 1 is just one example of a best-fit equation, and other best-fit equations may be used as would be readily apparent to one of ordinary skill in the art. The controller 110 and the camera 135 generally comprise a machine vision system that does not rely on a human operator to determine the level of the water volume in the sight glass 130. The controller 110 may analyze the change in pixilation of the captured images from the camera 135, and by using the known dimensions of the sight glass 130 or other calibration method, may compute a volume estimate of the water volume in sight glass 130. This calculation may be repeated as desired by selecting the time interval in which the camera 135 is to capture the images of the sight glass 130. Through the use of a best fit equation, the controller 110 may analyze the captured images as they are taken at the rate designated by the timer interval and provide a dynamic final volume estimate that updates as new images are captured. When this estimate stabilizes, the controller 110 may end the testing operation for the specific sample of drilling fluid undergoing the testing protocol. The stabilization of the final volume estimate may comprise selecting a variation range threshold between sequential final volume estimates or a series of final volume estimates such that if said threshold in variation between two or more final volume estimates (in any desired sequence) is not exceeded, the controller 110 may end the testing procedure.

Although the above describes the use of a machine vision system to determine the water volume measurement, it is to be understood that other processes may be used instead. For example, instead of a camera 135, the measurement of the water volume may be made by a scale that measures the water weight, floats (e.g., magnetic, visual, etc.) that illustrate the changes in the level of the water, displacers, differential pressure sensors, bubblers, capacitance level sensors, distance sensors (e.g., radar, laser, ultrasonic, etc.). Moreover, instead of a best-fit equation to estimate the water volume, the final water volume measurement may be estimated by other methods including, but not limited to, machine learning methods (e.g., neural networks, nearest neighbor, etc.), sigmoid functions (e.g., logistic function, hyperbolic tan, arctan, error function, Guidermannian function, etc.), and the like. As such, this disclosure expressly contemplates the use of other automated measurement systems in addition to or in place of the machine vision system and the best-fit estimation.

The controller 110 may conduct and/or perform the analysis of the water volume measurement test. The controller 110 may be coupled to the camera 135 and the heating element used to heat the sample test cell 105. The controller 110 may include a direct connection, a private network, a virtual private network, a local area network, a WAN (e.g., an Internet-based communication system), a wireless communication system (e.g., a satellite communication system, telephones), combinations thereof, or any other suitable communication link. The controller 110 may comprise any suitable data processing system, including computer systems, handheld devices, or any other suitable device. A suitable data processing system may include a processor, memory, and software operable on the processor to process and analyze the images generated by the camera 135, to adjust the parameters of the heating element, to operate any component of the cleaning process of the water retort apparatus 95, and/or to generally operate any part or the whole of the water retort apparatus 95. The controller 110 may optionally comprise a method and/or component for data storage, which may comprise any device suitable for storing data to be processed, including, but not limited to, compact disc drives, floppy drives, hard disks, flash memory, solid-state drives, and the like. Those of ordinary skill in the art will appreciate that suitable data processing systems may comprise additional, fewer, and/or different components than those described for the controller 110.

Data processing and analysis software used with the controller 110 may be used to analyze the images generated by the camera 135. This procedure may be automated such that the analysis happens without the need for operator input or control. Further, the operator may select from several previously input parameters or may be able to recall previously measured data. Any of the data may be transferable and/or storable on a USB or any other type of drive if desired.

The controller 110 may end the test by signaling to an operator that the test is complete and a final volume measurement for the water volume has been obtained. The operator may then initiate the cleaning process for the water retort apparatus 95. Alternatively, the controller 110 may initiate an automated cleaning process for the water retort apparatus 95. Further alternatively, the controller 110 may institute additional testing to determine the oil content of the oil in the sample of the drilling fluid as well as other analytical methods to examine other properties of the sample of the drilling fluid.

The cleaning process, whether automated or not, may comprise at least two operations. A plunger 140 may be used to eject the oil and suspended solids from the sample test cell 105. The plunger 140 may be automated or may be used by an operator to eject the oil and suspended solids from the sample test cell 105. The plunger 140 may comprise any plunger or plunging means sufficient for the pushing of the oil and suspended solids out of the sample test cell 105. In some examples, the sample test cell 105 may comprise the plunger 140 as an integrated component. The oil and suspended solids may be ejected into a separate collection container 145. The collection container 145 may hold the oil and suspended solids for subsequent testing if desired or may be a disposal container used to dispose of, or to convey for disposal, the oil and suspended solids. In automated embodiments, the controller 110 may control the operation of the plunger 140 and may initiate plunging of the sample test cell 105 after completion of a water volume test.

A gas container 150 may be connected to the tubing 125 through a valve 155, or other such selectively operable connection, and may eject a gas (e.g., nitrogen or other similar such gas) into the tubing 125, and optionally, into the condenser 120 and/or the sight glass 130. The gas may be any such gas for carrying away the liquid water from the tubing 125, and optionally the condenser 120 and/or the sight glass 130. In some optional embodiments, one or more of the tubing 125 and/or the condenser 120 and/or the sight glass 130 may comprise a hydrophobic coating on any of the surfaces that the liquid water may contact. The hydrophobic coating may reduce the time and gas needed to complete the cleaning process and, in some examples, may also reduce error in the water volume determination.

In some optional embodiments, an oil content test 160 may be conducted on the oil in the sample test cell 105 or in the collection container 145. If performed while the oil and suspended solids remain in the sample test cell 105, the oil content test 160 may be run before operation of the plunger 140. If run after conveyance of the oil and suspended solids to the collection container 145, subsequent samples of a drilling fluid may be run in the sample test cell 105 of the water retort apparatus 95 and the oil content test 160 may be initiated on the oil and the suspended solids in the collection container 145 at a desired time.

After completion of a water volume measurement of a specific sample of a drilling fluid, the controller 110 may initiate the cleaning process while maintaining the temperature of the heating element such that subsequent samples may be tested in quick succession without the need to ramp up the heating element. This may greatly speed up testing operations and allow for a quick succession of multiple drilling fluid sample tests. Alternatively, if additional testing is not desired, the controller 110 may be used, or may be automated, to shut down the heating element.

The optional oil content test 160 may be any such test sufficient for measuring the oil content of the oil and suspended solids from the sample of the drilling fluid. One example of the optional oil content test 160 may be a thermal conductivity test. The oil and suspended solids have different capabilities of conducting heat, and the thermal conductivity of the oil and the solids may be measured and compared with a calibration curve or other known baseline to determine the oil content or the relative changes to the oil content in the sample of drilling fluid. Thus, the thermal conductivity of the oil and suspended solids may be standardized, such that the measurement of the thermal conductivity of the oil and suspended solids may be taken and compared to this standardization to ascertain the oil content from the sample of drilling fluid. In some examples, these optional oil content tests 160 may be performed prior to conducting the water retort.

The thermal conductivity test may comprise the use of a thermal conductivity measuring apparatus such as a thermal conductivity probe. The thermal conductivity probe may be any thermal conductivity probe suitable for measuring the thermal conductivity of the oil and the suspended solids. The thermal conductivity probe may comprise a steady state probe and/or an unsteady state probe. Examples of the thermal conductivity probe may include, but are not to be limited to, needle probes, button probes, strip probes, plate sensors, and the like. Methods of measuring the thermal conductivity may include the divided bar method, transient plane source method, transient line source method, laser flash method, the 3ω-method, the time-domain thermoreflectance method, and any other suitable method.

The thermal conductivity probe may be inserted into the sample test cell 105 or the collection container 145 at any desired time. The heating element may be used to heat the sample test cell 105 or the collection container 145 to measure the thermal conductivity. In some optional examples, the thermal conductivity probe may be controlled by the controller 110. In some further optional examples, the actuation and use of the thermal conductivity probe may be automated and controlled by the controller 110.

Other optional oil content tests 160, as well as various other property tests, may be performed on the drilling fluid sample prior to or after use in the water retort apparatus 95 if desired. For example, a salinity measurement, a density measurement, or nuclear magnetic resonance testing, etc. may be performed on the drilling fluid sample and/or the oil and suspended solids as would be readily apparent to one of ordinary skill in the art. These additional tests may be used in conjunction with the water volume measurement to ascertain the oil to water ratio and/or the solids content of the sample of drilling fluid.

If the volume of oil is determined, the controller 110 may be used to determine an oil to water ratio for the sample of the drilling fluid. The oil to water ratio may be a useful determination for downstream processes such as solids control. Moreover, the oil to water ratio may be useful for adjusting the formulation of the drilling fluid to improve conformance with a target subterranean formation in an active drilling operation.

It should be clearly understood that the water retort apparatus 95 of FIG. 2 is merely one example of an application of the principles of this disclosure in practice, and a wide variety of other examples are possible. Therefore, the scope of this disclosure is not limited at all to the details of FIG. 2 described herein and/or depicted in any of the other FIGURES.

Figure 3:
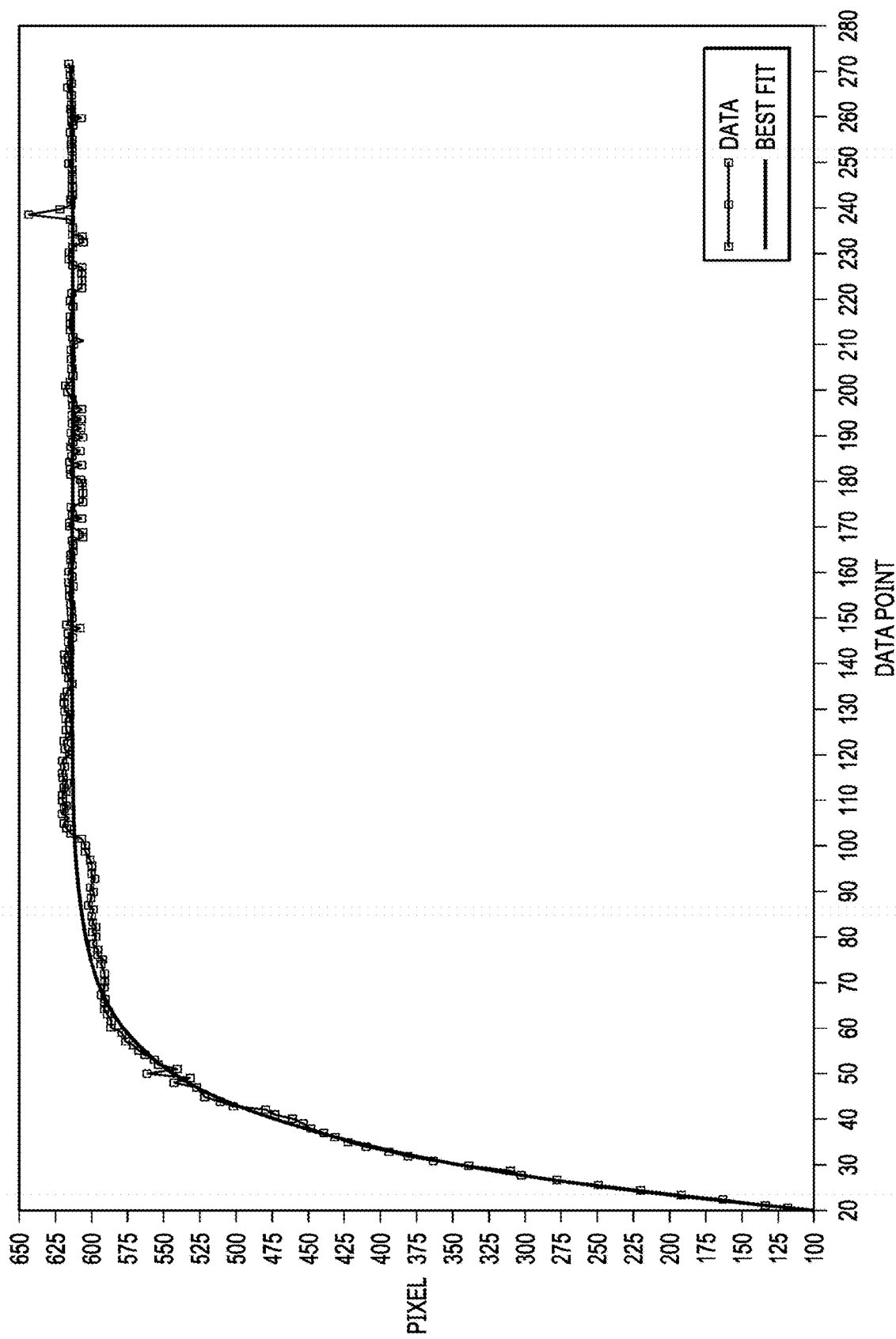
FIG. 3 illustrates an example graph of a final volume estimation of the water content of a drilling fluid sample in accordance with one or more examples described herein.

FIG. 3 illustrates an example water volume estimate graph produced by the controller (i.e., the controller 110 as illustrated in FIG. 2). The graph data may be obtained by conversion of the images captured by the camera (i.e., camera 135 as illustrated in FIG. 2) into a volume measurement which may be used in conjunction with a best-fit equation as described above to provide a final volume estimate. This process may be repeated as new images are captured by the camera 135. When the final volume estimate plateaus, the controller 110 may end the test in any desired manner as described above. The data may then be saved for use in downstream or upstream processes. Alternatively, the data may be combined with other sample data to provide other measurements such as the oil to water ratio of the sample of drilling fluid, which may also be used in upstream or downstream processes.

It should be clearly understood that the water volume estimate graph of FIG. 3 is merely one example of an application of the principles of this disclosure in practice, and a wide variety of other examples are possible. Therefore, the scope of this disclosure is not limited at all to the details of FIG. 3 described herein and/or depicted in any of the other FIGURES.

Figure 4:
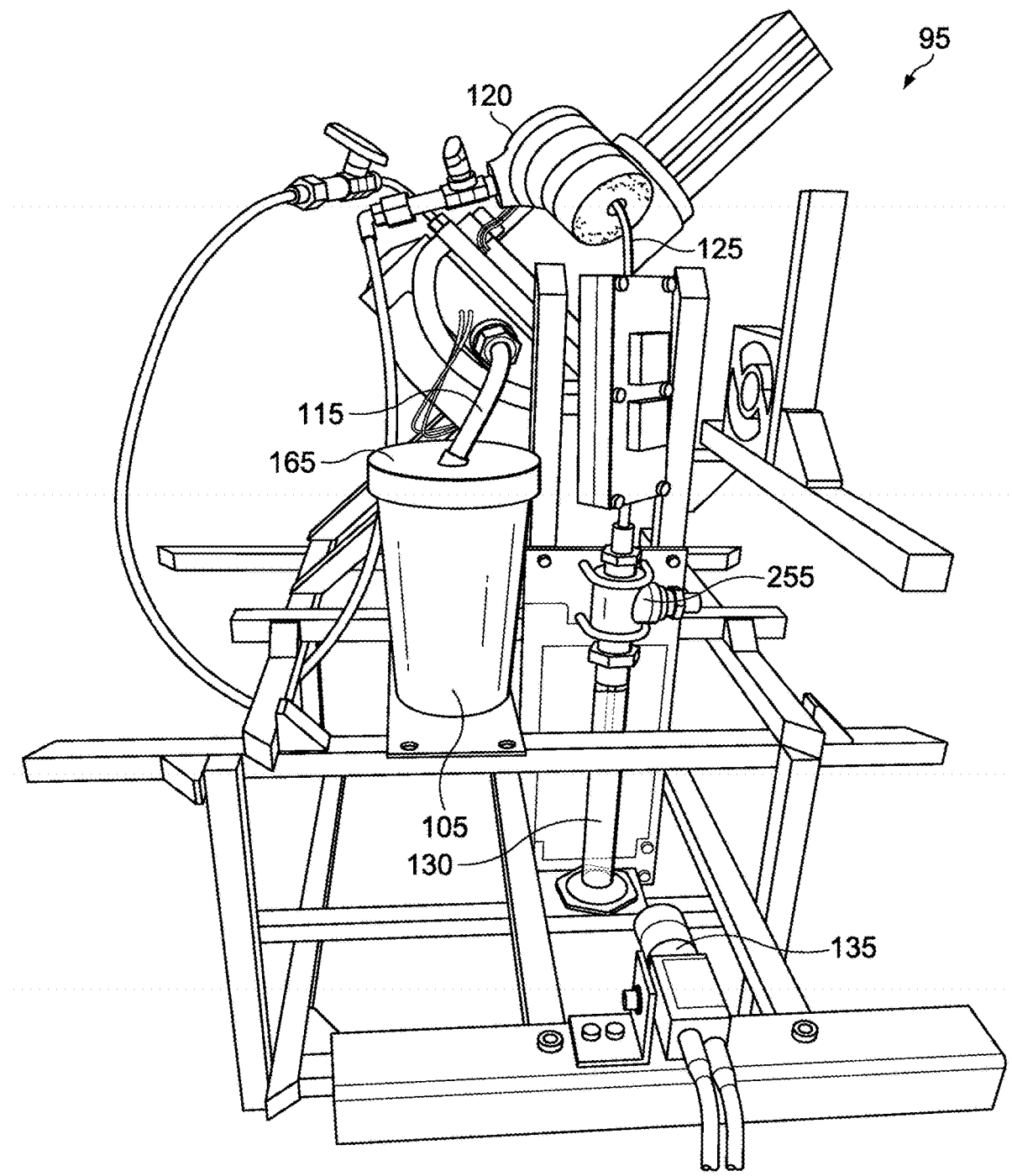
FIG. 4 is an isometric illustration of an example water retort apparatus in accordance with one or more examples described herein.

FIG. 4 is an isometric view of an example water retort apparatus 95. The sample test cell 105 is fitted with a threaded cap 165 that seals the sample test cell 105, preventing atmospheric leakage of the water vapor. The sample test cell 105 is heated, and the water vapor is flowed into tubing 115 where it may enter the insulated condenser 120. As the water vapor flows through the condenser 120 it condenses to its liquid phase and enters tubing 125 where it may drain into a sight glass 130. Images of the liquid water in the sight glass 130 may be captured by the camera 135. These images may be converted to volumetric data by a controller (not illustrated). When the water retort apparatus 95 is to be cleaned, a gas line may be inserted into valve 155 to inject a gas into tubing 125, and optionally the condenser 120 and the sight glass 130. A plunger (not illustrated) may be used to remove the oil and suspended solids from the sample test cell 105.

It should be clearly understood that the water retort apparatus 95 of FIG. 4 is merely one example of an application of the principles of this disclosure in practice, and a wide variety of other examples are possible. Therefore, the scope of this disclosure is not limited at all to the details of FIG. 4 described herein and/or depicted in any of the other FIGURES.

It is also to be recognized that the disclosed water retort apparatus, methods of use, and corresponding systems may also directly or indirectly affect the various downhole equipment and tools that may contact the water retort apparatus. Such equipment and tools may include, but are not limited to, wellbore casing, wellbore liner, completion string, insert strings, drill string, coiled tubing, slickline, wireline, drill pipe, drill collars, mud motors, downhole motors and/or pumps, surface-mounted motors and/or pumps, centralizers, turbolizers, scratchers, floats (e.g., shoes, collars, valves, etc.), logging tools and related telemetry equipment, actuators (e.g., electromechanical devices, hydromechanical devices, etc.), sliding sleeves, production sleeves, plugs, screens, filters, flow control devices (e.g., inflow control devices, autonomous inflow control devices, outflow control devices, etc.), couplings (e.g., electro-hydraulic wet connect, dry connect, inductive coupler, etc.), control lines (e.g., electrical, fiber optic, hydraulic, etc.), surveillance lines, drill bits and reamers, sensors or distributed sensors, downhole heat exchangers, valves and corresponding actuation devices, tool seals, packers, cement plugs, bridge plugs, and other wellbore isolation devices, or components, and the like. Any of these components may be included in the systems generally described above and depicted in FIGS. 1-4.

Provided is a water retort apparatus in accordance with the disclosure and the illustrated FIGS. An example water retort apparatus comprises a sample test cell, a heating element configured to heat the sample test cell to a temperature between about 212° F. and about 400° F., a condenser in fluidic communication with the sample test cell, a sight glass in fluidic communication with the condenser, a camera configured to capture images of the sight glass, and a controller configured to analyze the images captured by the camera and estimate a volume of water in the sight glass.

Additionally or alternatively, the water retort apparatus may include one or more of the following features individually or in combination. The water retort apparatus may further comprise a plunger within the sample test cell. The plunger may be configured to be actuated by the controller. The water retort apparatus may further comprise a valve coupled to a gas source. The valve may be configured to be actuated by the controller.

Provided is a method of measuring a water volume of a drilling fluid in accordance with the disclosure and the illustrated FIGS. An example method comprises providing a water retort apparatus comprising: a sample test cell, a heating element, a condenser in fluidic communication with the sample test cell, a sight glass in fluidic communication with the condenser, a camera, and a controller. The method further comprises placing a sample of the drilling fluid in the sample test cell, wherein the drilling fluid comprises water, oil, and suspended solids; heating the sample of the drilling fluid to a temperature sufficient to evaporate the water but not to a temperature sufficient to evaporate the oil; condensing the evaporated water in the condenser to provide liquid water; collecting the liquid water in the sight glass; capturing images of the liquid water in the sight glass with the camera; and analyzing the images of the liquid water to estimate the volume of water in the sight glass.

Additionally or alternatively, the method may include one or more of the following features individually or in combination. The method of claim may further comprise cleaning the sample test cell. The cleaning the sample test cell may be automated and may be initiated by the controller. The method may further comprise measuring an oil content of the oil and suspended solids. The oil content may be measured using a thermal conductivity probe. The method may further comprise calculating an oil to water ratio of the drilling fluid sample. The sample of the drilling fluid may be a first sample of the drilling fluid; wherein the method may further comprise measuring the water volume of a second sample of the drilling fluid; wherein the second sample of the drilling fluid may be introduced into the sample test cell while maintaining the heated temperature of the sample test cell. The method may further comprise flowing a gas through at least a portion of the water retort apparatus to remove the evaporated water or the liquid water from the water retort apparatus. The flowing of the gas may be automated and may be initiated by the controller. The method may further comprise measuring an oil content of the sample of the drilling fluid; wherein the oil is not vaporized by the measuring of the oil content of the sample of the drilling fluid. The water retort apparatus may further comprise a plunger within the sample test cell. The plunger may be configured to be actuated by the controller. The water retort apparatus may further comprise a valve coupled to a gas source. The valve may be configured to be actuated by the controller.

Provided is a system for measuring the water volume of a drilling fluid in accordance with the disclosure and the illustrated FIGS. An example system comprises a water retort apparatus comprising: a sample test cell, a heating element configured to heat the sample test cell to a temperature between about 212° F. and about 400° F., a condenser in fluidic communication with the sample test cell, a sight glass in fluidic communication with the condenser, a camera configured to capture images of the sight glass, and a controller configured to analyze the images captured by the camera. The system further comprises a drilling fluid comprising water, oil, and suspended solids.

Additionally or alternatively, the system may include one or more of the following features individually or in combination. The system may further comprise a thermal conductivity probe. The system may further comprise a plunger disposed within the sample test cell. The plunger may be configured to be actuated by the controller. The system may further comprise a valve coupled to a gas source. The valve may be configured to be actuated by the controller.

The preceding description provides various embodiments of the apparatuses, systems, and methods disclosed herein which may contain different method steps and alternative combinations of components. It should be understood that, although individual embodiments may be discussed herein, the present disclosure covers all combinations of the disclosed embodiments, including, without limitation, the different component combinations, method step combinations, and properties of the system.

It should be understood that the compositions and methods are described in terms of "comprising," "containing," or "including" various components or steps. The compositions and methods can also "consist essentially of" or "consist of" the various components and steps. Moreover, the indefinite articles "a" or "an," as used in the claims, are defined herein to mean one or more than one of the element that it introduces.

Therefore, the present embodiments are well adapted to attain the ends and advantages mentioned, as well as those that are inherent therein. The particular embodiments disclosed above are illustrative only, as the present invention may be modified and practiced in different but equivalent manners apparent to those skilled in the art having the benefit of the teachings herein. Although individual embodiments are discussed, the invention covers all combinations of all those embodiments. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative embodiments disclosed above may be altered or modified, and all such variations are considered within the scope and spirit of the present invention.

What is claimed is:

1. A water retort apparatus comprising:
   a sample test cell,
   a heating element configured to heat the sample test cell to a temperature between about 212° F. and about 400° F.,
   a condenser in fluidic communication with the sample test cell,
   a sight glass in fluidic communication with the condenser,
   a camera configured to capture images of the sight glass, and
   a controller configured to analyze the images captured by the camera and estimate a volume of water in the sight glass.

2. The water retort apparatus of claim 1, further comprising a plunger within the sample test cell.

3. The water retort apparatus of claim 2, wherein the plunger is configured to be actuated by the controller.

4. The water retort apparatus of claim 1, further comprising a valve coupled to a gas source.

5. The water retort apparatus of claim 4, wherein the valve is configured to be actuated by the controller.

6. A method of measuring a water volume of a drilling fluid, the method comprising:
   providing a water retort apparatus comprising:
      a sample test cell,
      a heating element,
      a condenser in fluidic communication with the sample test cell,
      a sight glass in fluidic communication with the condenser,
      a camera, and
      a controller;
   placing a sample of the drilling fluid in the sample test cell, wherein the drilling fluid comprises water, oil, and suspended solids;
   heating the sample of the drilling fluid to a temperature sufficient to evaporate the water but not to a temperature sufficient to evaporate the oil;
   condensing the evaporated water in the condenser to provide liquid water;
   collecting the liquid water in the sight glass;
   capturing images of the liquid water in the sight glass with the camera; and
   analyzing the images of the liquid water to estimate the volume of water in the sight glass.

7. The method of claim 6, further comprising cleaning the sample test cell.

8. The method of claim 7, wherein the cleaning the sample test cell is automated and is initiated by the controller.

9. The method of claim 6, further comprising measuring an oil content of the oil and suspended solids.

10. The method of claim 9, wherein the oil content is measured using a thermal conductivity probe.

11. The method of claim 10, further comprising calculating an oil to water ratio of the drilling fluid sample.

12. The method of claim 6, wherein the sample of the drilling fluid is a first sample of the drilling fluid; wherein the method further comprises measuring the water volume of a second sample of the drilling fluid; wherein the second sample of the drilling fluid may be introduced into the sample test cell while maintaining the heated temperature of the sample test cell.

13. The method of claim 6, further comprising flowing a gas through at least a portion of the water retort apparatus to remove the evaporated water or the liquid water from the water retort apparatus.

14. The method of claim 13, wherein the flowing of the gas is automated and is initiated by the controller.

15. The method of claim 6, further comprising measuring an oil content of the sample of the drilling fluid; wherein the oil is not vaporized by the measuring of the oil content of the sample of the drilling fluid.

16. A system for measuring the water volume of a drilling fluid, the system comprising:
   a water retort apparatus comprising:
      a sample test cell,
      a heating element configured to heat the sample test cell to a temperature between about 212° F. and about 400° F.,
      a condenser in fluidic communication with the sample test cell,
      a sight glass in fluidic communication with the condenser,
      a camera configured to capture images of the sight glass, and
      a controller configured to analyze the images captured by the camera; and a drilling fluid comprising water, oil, and suspended solids.

17. The system of claim 16, further comprising a thermal conductivity probe.

18. The system of claim 16, further comprising a plunger disposed within the sample test cell.

19. The system of claim 18, wherein the plunger is configured to be actuated by the controller.

20. The system of claim 16, further comprising a valve coupled to a gas source, wherein the valve is configured to be actuated by the controller.

* * * * *